United States Patent [19]

Schromm et al.

[11] Patent Number: 4,460,581
[45] Date of Patent: Jul. 17, 1984

[54] (1-HYDROXY-2-AMINO-ALKYL)-SUBSTITUTED BENZOXAZINONES AND BENZOXAZOLINONES

[75] Inventors: Kurt Schromm, Ingelheim am Rhein; Anton Mentrup, Mainz-Kastel; Ernst-Otto Renth, Ingelheim am Rhein; Armin Fügner, Gau-Algesheim, all of Fed. Rep. of Germany

[73] Assignee: Boehringer Ingelheim KG, Ingelheim am Rhein, Fed. Rep. of Germany

[21] Appl. No.: 433,681

[22] Filed: Oct. 12, 1982

[51] Int. Cl.³ .................. A61K 31/47; C07D 265/36
[52] U.S. Cl. ................... 424/244; 424/248.5; 424/248.54; 424/248.56; 424/263; 424/272; 260/330.8; 544/105; 546/275; 548/221
[58] Field of Search .............. 544/105; 548/221; 260/330.8; 546/275; 424/244, 248.5, 248.54, 248.56, 263, 272

[56] References Cited

U.S. PATENT DOCUMENTS 3,770,734 11/1973 Pesson et al. .................. 544/105
4,363,814 12/1982 Mentrup et al. ................ 424/272
4,378,361 3/1983 Schromm et al. ............... 544/105

FOREIGN PATENT DOCUMENTS 2429253 1/1976 Fed. Rep. of Germany .

OTHER PUBLICATIONS

Mentrup et al., Chemical Abstracts, vol. 84, (1976), 135683e.

Primary Examiner—Richard Raymond
Attorney, Agent, or Firm—Hammond & Littell, Weissenberger & Dippert

[57] ABSTRACT

Compounds of the formula

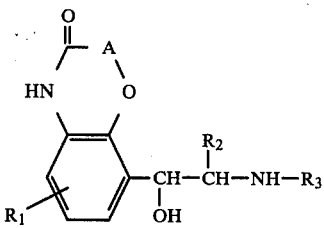

wherein A is a single bond,

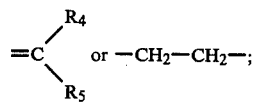

$R_1$ is —OH, —O—acyl, chlorine or hydrogen;
$R_2$ is hydrogen, methyl or ethyl;
$R_3$ is

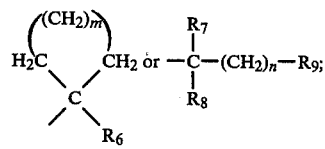

m is 2, 3 or 4;
n is 1, 2 or 3;
$R_4$ is hydrogen or lower alkyl;
$R_5$ is hydrogen, lower alkyl or, when $R_4$ is hydrogen, also phenyl;
$R_6$, $R_7$ and $R_8$ are each hydrogen or methyl;
$R_9$ is hydrogen, —Ar, —OAr or —NH—CO—Ar;
Ar is

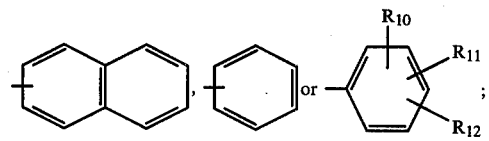

$R_{10}$, $R_{11}$ and $R_{12}$ which may be identical to or different from each other, are each hydrogen, hydroxyl, methyl, methoxy, halogen, methylenedioxy, —NH—$R_{13}$ or —$CONH_2$; and
$R_{13}$ is hydrogen, acyl or lower alkylsulfonyl;

and non-toxic, pharmaceutically acceptable acid addition salts thereof; the compounds as well as their salts are useful for the treatment of asthma, bronchitis, urticaria, conjunctivities, hay fever, colds and cardiovascular disorders, and for relaxation of the uterine musculature.

6 Claims, No Drawings

(1-HYDROXY-2-AMINO-ALKYL)-SUBSTITUTED BENZOXAZINONES AND BENZOXAZOLINONES

This invention relates to novel derivatives of benzoxazinone and benzoxazolinone and acid addition salts thereof, to methods of preparing these compounds, to pharmaceutical compositions containing them as active ingredients, and to methods of using them for the treatment of asthma, bronchitis, urticaria, conjunctivitis, hay fever, colds and cardiovascular disorders, and for relaxation of the uterine musculature.

More particularly, the present invention relates to a novel class of compounds represented by the formula

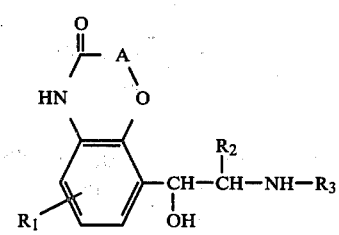

wherein A is a single bond,

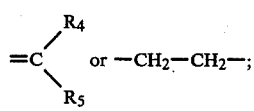

$R_1$ is —OH, —O—acyl, chlorine or hydrogen;
$R_2$ is hydrogen, methyl or ethyl;
$R_3$ is

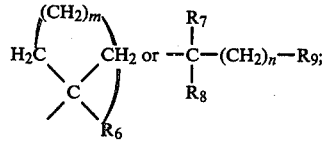

m is 2,3 or 4;
n is 1,2 or 3;
$R_4$ is hydrogen or lower alkyl;
$R_5$ is hydrogen, lower alkyl or, when $R_4$ is hydrogen, also phenyl;
$R_6$, $R_7$ and $R_8$ are each hydrogen or methyl;
$R_9$ is hydrogen, —Ar, —OAr or —NH—CO—Ar;
Ar is

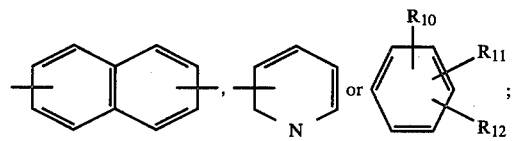

$R_{10}$, $R_{11}$ and $R_{12}$ which may be identical to or different from each other, are each hydrogen, hydroxyl, methyl, methoxy, halogen, methylenedioxy, —NH—$R_{13}$ or —CONH$_2$; and
$R_{13}$ is hydrogen, acyl or lower alkylsulfonyl;
and non-toxic, pharmaceutically aceceptable acid addition salts thereof, in the form of then racemates, enantiomers or diastereisomeric pairs of enantiomers.

The term "lower alkyl" refer to alkyl of 1 to 4 carbon atoms. "Halogen" refers to flourine, chlorine, bromine and iodine, preferably fluorine and chlorine. "Acyl" refers to optionally substituted straight or branched aliphatic carboxylic acid radicals of up to 6 carbon atoms or optionally substituted benzoyl.

A preferred subgenus is constituted by compounds of the formula I wherein A is a single bond, —CH$_2$—, —CH(CH$_3$)—, —C(CH$_3$)$_2$— or —CH(C$_2$H$_5$)—;
$R_1$ is —OH or —O—acyl in the m- or p-position relative to the side chain;
$R_2$ is hydrogen, methyl or ethyl;
$R_3$ is

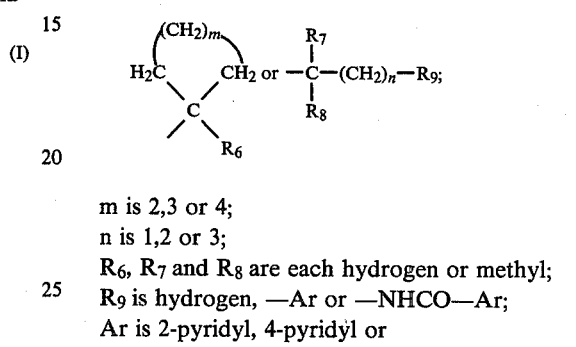

m is 2,3 or 4;
n is 1,2 or 3;
$R_6$, $R_7$ and $R_8$ are each hydrogen or methyl;
$R_9$ is hydrogen, —Ar or —NHCO—Ar;
Ar is 2-pyridyl, 4-pyridyl or

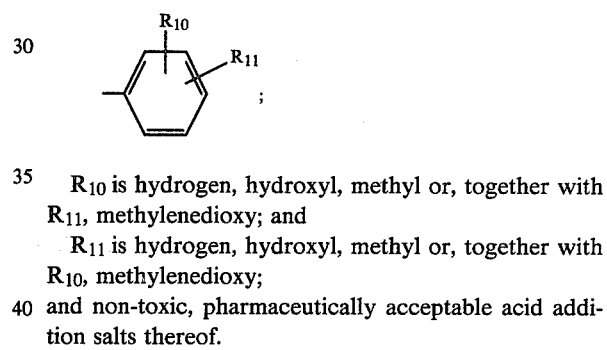

$R_{10}$ is hydrogen, hydroxyl, methyl or, together with $R_{11}$, methylenedioxy; and
$R_{11}$ is hydrogen, hydroxyl, methyl or, together with $R_{10}$, methylenedioxy;
and non-toxic, pharmaceutically acceptable acid addition salts thereof.

An especially preferred subgenus is constituted by those compounds of the formula I wherein A is —C(CH$_3$)$_2$— or —CH$_2$—;
$R_1$ is hydroxyl in the m- or p-position relative to the side chain;
$R_2$ is hydrogen, methyl or ethyl;
$R_3$ is isopropyl, tert. butyl, cyclopentyl, 1-methylcyclopentyl or

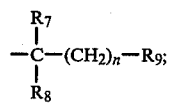

n is 1 or 2;
$R_7$ and $R_8$ are each hydrogen or methyl; and
$R_9$ is phenyl, 2-hydroxy-phenyl, 4-hydroxy-phenyl, 2-pyridyl, 4-pyridyl,

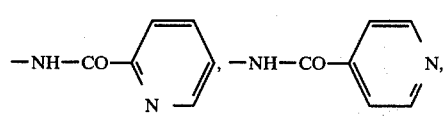

-continued

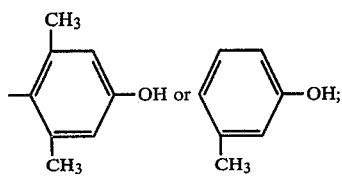

and non-toxic, pharmaceutically acceptable acid addition salts thereof.

The compounds embraced by formula I may be prepared the following known methods:

Method A

By reducing a compound of the formula

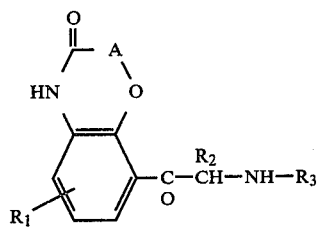
(II)

wherein A, $R_1$, $R_2$ and $R_3$ have the meanings previously defined, but wherein phenolic OH-groups protected by a hydrogenolytically removable group may also be present.

The reduction is effected in a solvent which is sufficiently stable under the reaction conditions, for instance in a lower alkanol such as ethanol. Hydrogen and hydrogenation catalysts, such as palladium, platinum or Raney nickel, or hydrides such as sodium borohydride or diborane may be used as the reducing agent. By a suitable choice of reducing agent (catalytic reduction or reduction with hydrides) it is possible to prepare predominantly the erythro or threo form. Any hydrogenolytically removable protective groups present at the central amino group or at a phenolic hydroxyl group, such as benzyl or substituted benzyl, may be removed in the usual way during or after the reduction.

The starting compounds of the formula II, which are also novel, may be prepared by known methods, as shown by the following reaction sequences, for example, where Bz=benzyl and Ph=phenyl:

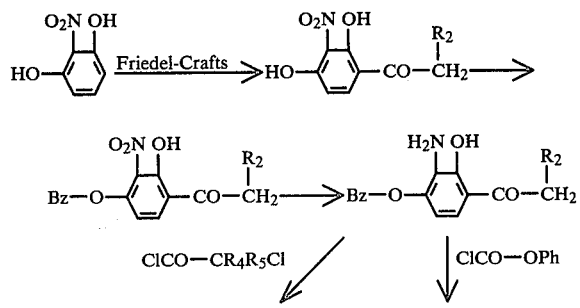

-continued

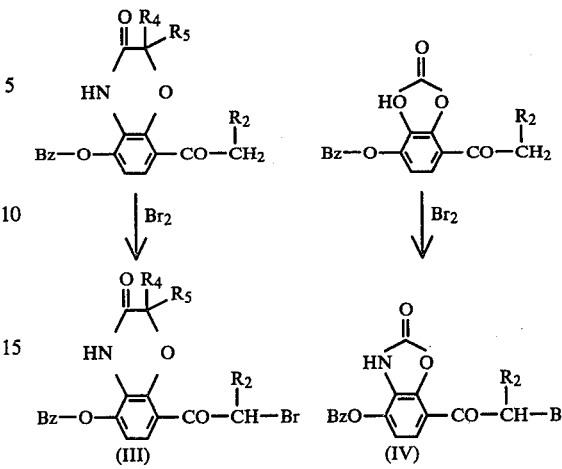

Corresponding bromoketones with the (protected) OH-group in the m-position relative to the side-chain may be obtained as follows:

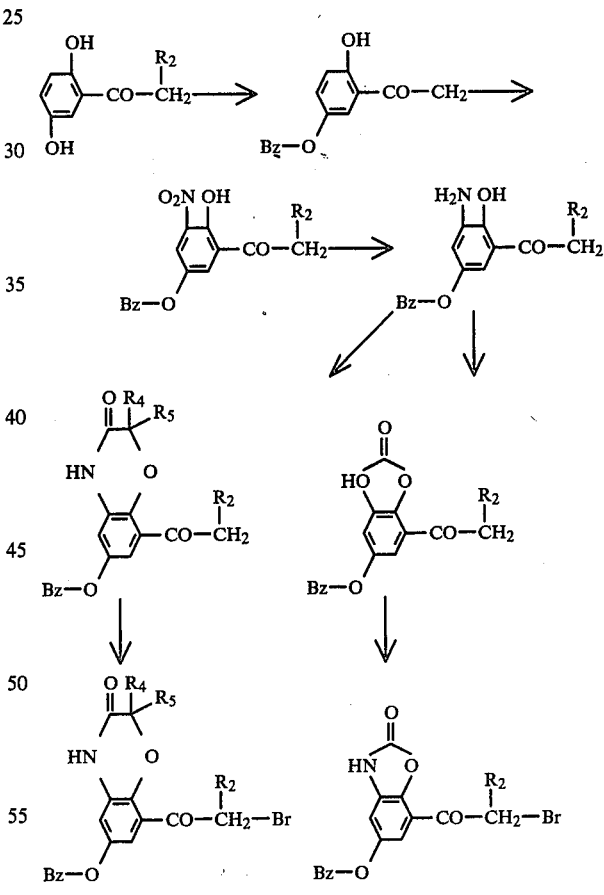

The bromoketones of the formula

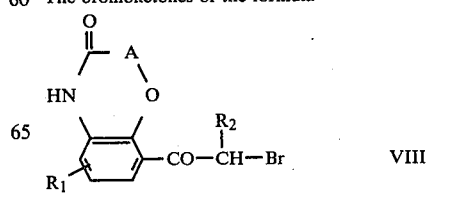
VIII obtained in this way or by other conventional methods, wherein A, $R_1$ and $R_2$ have the meanings previously defined, but wherein phenolic OH-groups protected by hydrogenolytically removable groups such as benzyl can be present, can react with an amine of the formula

(VIII)

wherein $R_3$ is as hereinbefore defined and R' represents hydrogen or a hydrogenolytically removable group, such as benzyl or substituted benzyl to compounds of formula

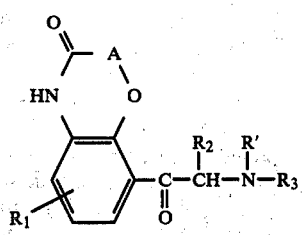
(IIa)

wherein A, $R_1$, $R_2$ and R' are as hereinbefore defined. The reaction is carried out in a suitable inert solvent such as acetonitrile or ethyl acetate, in the presence of an acid-binding agent such as sodium carbonate or an excess of the amine. Any protective groups present in the reaction product may be removed subsequently or as the reaction continues or afterwards.

Method B

By reaction of a phenylglyoxal or hemiacetal of the formula

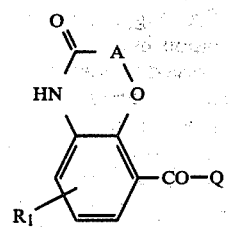
(IX)

wherein $R_1$ and A have the meanings previously defined, and Q is —CHO or

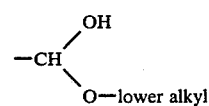

with an amine of the formula $H_2N—R_3$ (X)

wherein $R_3$ has the meanings previously defined, under the conditions of reductive amination.

Instead of reactants IX and X, it is also possible to subject a Schiff's base of the formula

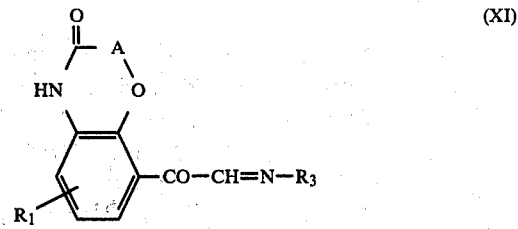
(XI)

wherein A, $R_1$ and $R_3$ have the meanings previously defined, which may occur as an intermediate, to reduction.

Complex hydrides, preferably sodium borohydride or hydrogen and hydrogenation catalysts such as platinum, palladium or nickel are used as the reducing agent.

Any phenolic hydroxyl groups contained in the starting material may be protected by means of conventional hydrogenolytically removable groups. These protective groups may be removed by hydrogenolysis in the usual way during or after the reduction.

End products are obtained wherein $R_2$ is hydrogen.

The starting compounds of the formula IX may be obtained from acetophenone derivatives of the formula

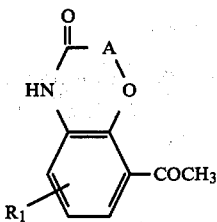
(XII)

wherein $R_1$ and A have the meanings previously defined, by oxidation with selenium dioxide in aqueous dioxane. Depending on whether the product is crystallized from water or a lower alkanol, glyoxals or hemiacetals are obtained.

Amines of formula X are known or may readily be obtained by conventional methods.

Method C

By removing hydrogenolytically removable protective groups from a compound of the formula

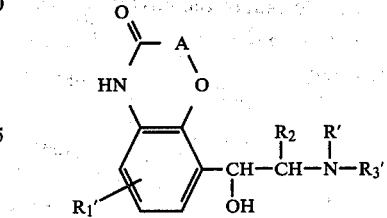
(XIII)

which can be obtained by reduction of compounds of formula (II) or (IIa) as described under method A, wherein A and $R_2$ have the meanings previously defined, $R_1'$ is $R_1$ or an OH- group protected by a hydrogenolytically removable protective group, $R_3'$ is $R_3$, but any OH- group contained in $R_3$ may be protected by a hydrogenolytically removable protective group, and R' is hydrogen or a hydrogenolytically removable protective group. Examples of hydrogenolytically removable protective groups include, in particular, benzyl and substituted benzyl.

If desired, the compounds obtained according to methods A to C may be separated into their enantiomers or diastereoisomeric pairs of enantiomers by conventional methods; bases initially obtained may be converted into acid addition salts, and acid addition salts initially obtained may be converted into bases or salts of other acids.

Examples of non-toxic, pharmaceutically acceptable acid addition salts are those formed with hydrochloric acid, hydrobromic acid, sulfuric acid, methanesulfonic acid, formic acid, fumaric acid or the like.

The following examples illustrate the present invention and will enable others skilled in the art to understand it more completely. It should be understood, however, that the invention is not limited solely to the particular examples given below.

Depending upon the solvent from which the end products of these examples were crystallized, some of them still contained defined quantities of the solvent in the crystal. The melting points given are uncorrected.

EXAMPLE 1

Erythro-5'-hydroxy-8'-(1-hydroxy-2-isopropylamino-butyl)-2H-1,4-benzoxazin-3-(4H)-one hydrochloride hydrate by method A

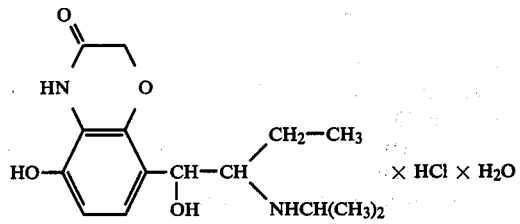

16.1 gm of 5'-benzyloxy-8'-(1-oxo-2-bromo-butyl)-2H-1,4-benzoxazin-3-(4H)-one and 7.5 gm of isopropylamine were stirred in 100 ml of acetonitrile for 4 hours at 60° C. After acidification with concentrated hydrochloric acid and addition of the mixture to 100 ml of water, 5'-benzyloxy-8'-(1-oxo-2-isopropylamino-butyl)-2H-1,4-benzoxazin-3(4H)-one hydrochloride (melting point 229°–232° C.) crystallized out.

6 gm of this compound were debenzylated in methanol in the presence of palladium-on-charcoal as the catalyst to yield 5'-hydroxy-8'-(1-oxo-2-isopropylamino-butyl)-2H-1,4-benzoxazine-3-(4H)-one hydrochloride dihydrate (melting point 242°–245° C.).

By hydrogenating 3.3 gm of this compound in methanol with platinum as the catalyst, 3 gm of erythro-5'-hydroxy-8'-(1-hydroxy-2-isopropylamino-butyl)-2H-1,4-benzoxazin-3-(4H)-one hydrochloride hydrate were obtained (yield: 90% of theory), which melted at 208°–210° C.

EXAMPLE 2

Threo-5'-hydroxy-8'-(1-hydroxy-2-isopropylamino-butyl)-2H-1,4-benzoxazin-3-(4H)-one hydrochloride by method C

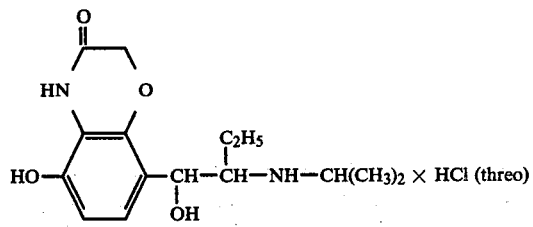

A mixture of 32.4 gm of 5'-benzyloxy-8'-(1-oxo-2-bromo-butyl)-2H-1,4-benzoxazin-3-(4H)-one and 72 gm of benzylisopropylamine was stirred at 100° C. for 15 hours. After the addition of water, the oil which precipitated was taken up in ether, and the solution was diluted with petroleum ether. 5'-Benzyloxy-8'-(1-oxo-2-benzylisopropylamino-butyl)-2H-1,4-benzoxazin-3-(4H)-one crystallized out.

11.6 gm of this compound were combined in a mixture of 60 ml of ethanol and 60 ml of acetonitrile with 1 gm of sodium borohydride, and the resulting mixture was stirred for three hours. Then, 250 ml of ice-cold water and 100 ml of ethyl acetate were added and, after the sodium borohydride had been decomposed with concentrated acetic acid while stirring, the mixture was made alkaline by the addition of concentrated ammonia, and the ethyl acetate phase was separated, dried and evaporated in a rotary evaporator. The oily residue was dissolved in ether, the solution was cooled, and the precipitated threo-5'-benzyloxy-8'-(1-hydroxy-2-benzylisopropylamino-butyl)-2H-1,4-benzoxazin-3-(4H)-one (melting point 89°–92° C.) was suction-filtered off.

4.8 gm of this compound were hydrogenated in 100 ml of methanol with palladium-on-charcoal as the catalyst. After the uptake of hydrogen had ceased, the catalyst was removed by suction-filtering, the mother liquor was concentrated by evaporation in a rotary evaporation, the oily residue was dissolved in acetone/ethanol, and the solution was acidified with the calculated quantity of hydrochloric acid. The acid solution was diluted with ether, and the precipitated threo-5'-hydroxy-8'-(1-hydroxy-2-isopropylamino-butyl)-2H-1,4-benzoxazin-3-(4H)-one hydrochloric (yield: 74% of theory) was suction-filtered off, after re-precipitation from methanol/ether it melted at 202°–205° C.

EXAMPLE 3

5'-Hydroxy-8'-(1-hydroxy-2-tert.butylamino-ethyl)-2H-1,4-benzoxazin-3-(4H)-one hydrochloride by method C

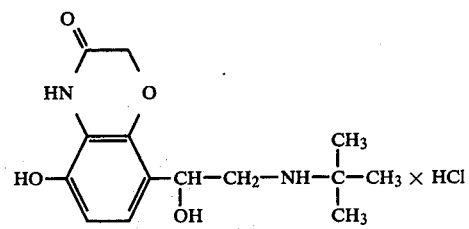

A mixture of 10 gm of 5'-benzyloxy-8'-(1-oxo-2-bromoethyl)-2H-1,4-benzoxazin-3-(4H)-one and 8.75 gm of benzyltert. butylamine was refluxed in 100 ml of acetonitrile for 3 hours. After cooling, the precipitated crystals were suction-filtered off and washed with 200 ml of warm water. The crystals were then acidified in acetonitrile with ethereal hydrochloric acid; after dilution with ethyl acetate, 5'-benzyloxy-8'-(1-oxo-2-benzyl-tert. butylaminoethyl)-2H-1,4-benzoxazin-3-(4H)-one hydrochloride precipitated (melting point 185°–189° C.).

7 gm of this compound were debenzylated at 5 bar and at 50° C. in 100 of methanol, in the presence of palladium-on-charcoal as the catalyst, to yield 5'-hydroxy-8'-(1-oxo-2-tert. butylamino-ethyl)-2H-1,4-benzoxazin-3-(4H)-one hydrochloride (melting point 237°–240° C.).

By catalytic hydrogenation of 2.2 gm of this compound in methanol in the presence of platinum, 1.6 gm of 5'-hydroxy-8'-(1-hydroxy-2-tert. butylamino-ethyl)-2H-1,4-benzoxazin-3-(4H)-one hydrochloride were obtained (yield: 72.5% of theory); melting point 185°–187° C.

Using procedures analogous to those described in Examples 1 to 3, the following compounds of the formula I were also prepared:

TABLE I

| Example No. | A | $R_1$ | $R_2$ | $R_3$ | Yield % | Salt with | M.P. °C. |
|---|---|---|---|---|---|---|---|
| 4 | —CH$_2$— | 5-OH | —C$_2$H$_5$ | —C(CH$_3$)$_3$ | 66 | HCl × 2 H$_2$O | 230 (decomp.) |
| 5 | —CH$_2$— | 6-OH | —C$_2$H$_5$ | —CH(CH$_3$)$_2$ | 63 | HCl | 163–165 |
| 6 | —CH$_2$— | 6-OH | —C$_2$H$_5$ | —C(CH$_3$)$_3$ | 83 | HCl | 259–261 |
| 7 | single bond | 4-OH | —C$_2$H$_5$ | —CH(CH$_3$)$_2$ | 67 | HCl | 230–232 |
| 8 | single bond | 5-OH | —C$_2$H$_5$ | —CH(CH$_3$)$_2$ | 71 | HCl × 1 H$_2$O | 257–259 |
| 9 | —CH$_2$— | 5-OH | —CH$_3$ | —CH(CH$_3$)$_2$ | 88 | HCl × ½ H$_2$O | 244 |
| 10 | —CH$_2$— | 5-OH | —C$_2$H$_5$ | cyclopentyl | 86 | HCl × ½ H$_2$O | 243–245 |
| 11 | —CH$_2$— | 5-OH | —C$_2$H$_5$ | —CH$_2$—CH$_2$—C$_6$H$_4$—OH | 73.5 | HCl | 206–209 |
| 12 | —CH$_2$— | 5-OH | —C$_2$H$_5$ | —CH$_2$—CH$_2$—O—C$_6$H$_4$(CONH$_2$) | 52 | HCl | 170–173 |
| 13 | —CH$_2$— | 5-OH | —C$_2$H$_5$ | —CH(CH$_3$)—CH$_2$—C$_6$H$_4$—OH | 64 | CH$_3$SO$_3$H × H$_2$O | 197–201 |
| 14 | —CH$_2$— | 5-OH | —C$_2$H$_5$ | —CH$_2$—CH$_2$—C$_6$H$_4$—NH—SO$_2$CH$_3$ | 83 | CH$_3$SO$_3$H | 187–190 |
| 15 | —CH$_2$— | 5-OH | —C$_2$H$_5$ | —CH$_2$—CH$_2$—C$_6$H$_4$—NH—C(O)—CH$_3$ | 54 | HCl | 208–211 |
| 16 | —CH$_2$— | 5-OH | —H | —C(CH$_3$)$_2$—CH$_2$—C$_6$H$_4$—NH$_2$ | 70 | HCl | 155–159 |
| 17 | —CH$_2$— | 5-OH | —C$_2$H$_5$ | —CH$_2$—CH$_2$—C$_6$H$_3$(C$_2$H$_5$)—OH | 90 | HCl, CH$_3$SO$_2$H × H$_2$O | 234–236, 92–94 |
| 18 | —CH$_2$— | 5-O—C(O)—C(CH$_3$)$_3$ | —C$_2$H$_5$ | —CH(CH$_3$)$_2$ | | | |
| 19 | —CH$_2$— | 5-O—C(O)—C$_6$H$_4$—CH$_3$ | —C$_2$H$_5$ | —CH(CH$_3$)$_2$ | | | |
| 20 | —CH$_2$— | 5-OH | —C$_2$H$_5$ | cyclohexyl | 90 | HCl, CH$_3$SO$_3$H × H$_2$O | 234–236, 92–94 |

EXAMPLE 21

5'-Hydroxy-8'-[1-hydroxy-2-(4-phenyl-2-methyl-butylamino)-ethyl]-2H-1,4-benzoxazin-3-(4H)-one hydrochloride by method B A mixture of 5 gm of 5'-benzyloxy-8'-(1-oxo-2-hydroxy-2-ethoxy-ethyl)-2H-1,4-benzoxazin-3-(4H)-one, 2.2 gm of 1,1-dimethyl-3-phenyl-propylamino and 50 ml of alcohol was heated at 50°–60° C. for 3 hours. After the reaction mixture had been cooled, the Schiff's base precipitated thereby (melting point 138°–140° C.) was suction-filtered off.

4.5 gm of this compound were added to 100 ml of alcohol and mixed with 1 gm of sodium borohydride, and the mixture was stirred for 2 hours at room temperature. After the addition of 100 ml of water, 5'-benzyloxy-8'-[1-hydroxy-2-(4-phenyl-2-methyl-butylamino)-ethyl]-2H-1,4-benzoxazin-3-(4H)-one precipitated (melting point 162°–164° C.); it was suction-filtered off, and the hydrochloride (melting point 205°–207° C.) was prepared with ethereal hydrochloric acid.

By cataytic hydrogenation of this compound in 50 ml of methanol under normal conditions, using palladium-on-charcoal as the catalyst, 2.7 gm of 5'-hydroxy-8'-[1-hydroxy-2-(4-phenyl-2-methyl-butylamino)-ethyl]-2H-1,4-benzoxazin-3-(4H)-one hydrochloride were obtained (melting point 159°–161° C.; yield: 90% of theory).

EXAMPLE 22

6'-Chloro-8'-[1-hydroxy-2-(tert.butylamino)-ethyl]-2H-1,4-benzoxyazin-3-(4H)-one hydrochloride by method B

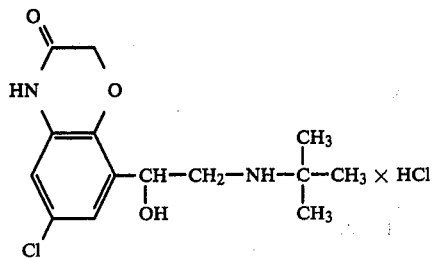

A mixture of 5.8 gm of 6'-chloro-8'-(1-oxo-2-hydroxy-2-ethoxy-ethyl)-2H-1,4-benoxazin-3-(4H)-one, 1.5 gm of tert.butylamine, 60 of dioxane and 60 ml of alcohol was heated at 50° C. for 2 hours. The reaction solution was then cooled, and 2 gm of sodium borohydride were added thereto at 10° to 20° C. The solution was stirred at room temperature for 1 hour, then poured into 500 ml of ice-cold water, and 150 ml of ethyl acetate were added. After the sodium borohydride had been decomposed with concentrated acetic acid while stirring, the mixture was made alkaline with aqueous ammonia, and the ethyl acetate phase was separated, dried with sodium sulfate and evaporated in a rotary evaporator. The oily residue was dissolved in 15 of alcohol, the solution was acidified with ethereal hydrochloric acid, and the 6'-chloro-8'-[1-hydroxy-2-(tert.butylamino)-ethyl]-2H-1,4-benzoxazin-3-(4H)-one hydrochloride precipitated thereby (yield: 38% of theory) was suction-filtered off. After being re-precipitated twice from methanol in the presence of activated charcoal, the hydrochloride had a melting point above 300° C. (melting point of base: 173°–177° C.).

Using procedures analogous to those described in Examples 21 and 22, the following compounds of the formula I were also prepared:

TABLE II

| Example No. | A | $R_1$ | $R_2$ | $R_3$ | Yield % | Salt with | M.P. °C. |
|---|---|---|---|---|---|---|---|
| 23 | —CH$_2$— | —H | —H | —C(CH$_3$)$_3$ | | | |
| 24 | —CH$_2$— | -5-OH | —H | —C(CH$_3$)$_3$ | | | |
| 25 | —C(CH$_3$)$_2$ | 5-OH | —H | —C(CH$_3$)$_3$ | | | |
| 26 | single bond | 5-OH | —H | —C(CH$_3$)$_2$—CH$_2$—CH$_2$—C$_6$H$_4$—F | 42 | HCl × ½ H$_2$O | 155–160 |
| 27 | —CH$_2$— | 6-OH | —H | (cyclopropyl with H, H$_3$C) | 52 | HCl | 226–229 |
| 28 | —CH$_2$— | 6-OH | —H | —CH(CH$_3$)—CH$_2$—C$_6$H$_4$—OH | 16 | HCl | 206–209 |
| 29 | single bond | 5-OH | —H | —C(CH$_3$)$_3$ | 26 | HCl × 1 CH$_3$CN | indefinite 195° C. decomp. |

TABLE II-continued

| Example No. | A | $R_1$ | $R_2$ | $R_3$ | Yield % | Salt with | M.P. °C. |
|---|---|---|---|---|---|---|---|
| 30 | —CH$_2$— | 5-OH | —H | —CH(CH$_3$)—CH$_2$—⌬—OH | 42 | HCl × 1 CH$_3$OH | 130–133 |
| 31 | —CH$_2$— | 5-OH | —H | —C(CH$_3$)$_2$—CH$_2$CH$_2$—⌬ (OH) | 42 | HCOOH × H$_2$O | 120–124 |
| 32 | —CH$_2$— | 5-OH | —H | —C(CH$_3$)$_2$—CH$_2$—naphthyl | 40 | CH$_3$SO$_3$H | 192–195 |
| 33 | —CH$_2$— | 5-OH | —H | —C(CH$_3$)$_2$—CH$_2$—CH$_2$—O—⌬ (H$_2$NOC) | 35 | HCl | 205–208 |

EXAMPLE 34

6'-Hydroxy-8'-(1-hydroxy-2-ethylamino-ethyl)-2H-1,4-benzoxazin-3-(4H)-one hydrochloride by method C

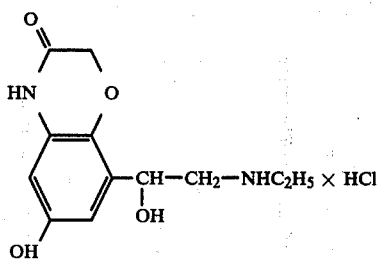

4.3 gm of 6'-benzyloxy-8'-(1-hydroxy-2-benzylethylamino-ethyl)-2H-1,4-benzoxazin-3-(4H)-one hydrochloride (melting point 232°–235° C.) were hydrogenated in 125 ml of methanol in the presence of 0.5 gm of 5% palladium-on-charcoal. After the calculated amount of hydrogen had been absorbed, the catalyst was filtered off, and the solution was distilled under reduced pressure. By triturating the residue with acetonitrile, 2.5 gm of 6'-hydroxy-8'-(1-hydroxy-2-ethylamino-ethyl)-2H-1,4-benzoxazin-3-(4H)-one hydrochloride were obtained (yield: 86.7% of theory), which melted at 240° to 242° C. after being re-precipitated from emthanol/ether.

EXAMPLE 35

4'-Hydroxy-7'-[1-hydroxy-2-(4-picolinic acid amido-2-methyl-2-butylamino)-ethyl]-2-benzoxazolinon-2-one formate by method C

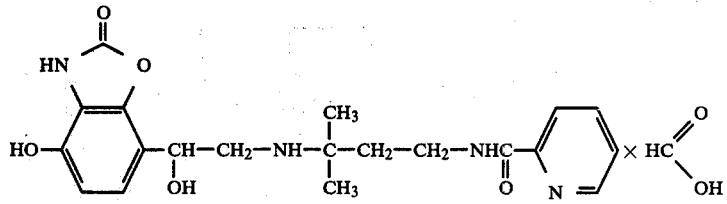

6.3 gm of 4'-benzyloxy-7'-[1-hydroxy-2-(4-picolinic acid-amino-2-methyl-2-butylamino)-ethyl]-2-benzoxazolinone (melting point 130°–133° C.) were hydrogenated in 125 ml of methanol in the presence of 1 gm of 5% palladium-on-charcoal. When the uptake of hydrogen had ceased the catalyst was filtered off, and the clear solution was evaporated in a rotary evaporator under reduced pressure. The oily residue was dissolved in 10 ml of ethanol, and 0.58 gm of formic acid were added. After 5 hours, the 4'-hydroxy-7'-[1-hydroxy-2-(4-picolinic acid amido-2-methyl-2-butylamino)-ethyl]-2-benzoxazolinone formate which had precipitated (yield: 78.5% of theory, melting point 166°–168° C.) was suction-filtered off.

Using procedures analogous to those described in examples 34 and 35, the following compounds of the formula I were also prepared:

TABLE III

| Example No. | A | $R_1$ | $R_2$ | $R_3$ | Yield % | Salt with | M.P. °C. |
|---|---|---|---|---|---|---|---|
| 36 | $-C(CH_3)_2-$ | 5-OH | -H | $-C(CH_3)_3$ | 87 | HCl × 1 $C_2H_5OH$ | 205–208 |
| 37 | $-CH_2-$ | 6-OH | -H | $-C(CH_3)_3$ | 75 | HCl × 1 $C_2H_5OH$ | 246–247 |
| 38 | $-CH_2-$ | 6-OH | -H | $-C(CH_3)_2-CH_2-CH_2-$C$_6$H$_5$ | 70 | HCl × 1 $C_2H_5OH$ | 120–123 |
| 39 | single bond | 4-OH | -H | $-C(CH_3)_2-$C$_6$H$_5$ | 70 | HCOOH × 1 $H_2O$ | 189–192 |
| 40 | $-CH_2-$ | 6-OH | -H | 1-methylcyclopentyl | 88 | HCl | 226–229 |
| 41 | $-CH_2-$ | 6=OH | -H | $-CH(CH_3)-CH_2-$(4-hydroxyphenyl) | 78.5 | HCl | 206–209 |
| 42 | single bond | 4-OH | -H | $-C(CH_3)_2-CH_2-CH_2-$C$_6$H$_5$ | 75 | HCl | 174–175 |
| 43 | single bond | 4-OH | -H | $-C(CH_3)_2-CH_2-CH_2-$(4-F-C$_6$H$_4$) | 90 | HCl × ½ $H_2O$ | 155–160 |
| 44 | single bond | 4-OH | -H | $-C(CH_3)_2-CH_2-CH_2-$(2-pyridyl) | 75 | ½ HOOCC=HCCOOH | 175–178 Base:170–173 |
| 45 | single bond | 4-OH | -H | $-C(CH_3)_2-CH_2-CH_2-$(4-pyridyl) | 60 | HCl | 143–146 |
| 46 | single bond | 4-OH | -H | $-C(CH_3)_3$ | 76 | HCl × 1 $CH_3CN$ | indefinite 195 decomp. |

TABLE III-continued

| Example No. | A | $R_1$ | $R_2$ | $R_3$ | Yield % | Salt with | M.P. °C |
|---|---|---|---|---|---|---|---|
| 47 | $-CH_2-$ | 6-OH | $-H$ | 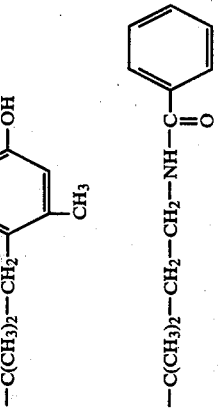 $-C(CH_3)_2-CH_2-$ (3,5-dimethyl-4-OH-phenyl) | 91 | $CH_3SO_3H \times 1\ H_2O$ | 252–254 |
| 48 | $-CH_2-$ | 5-OH | $-H$ |  $-C(CH_3)_2-CH_2-CH_2-NH-C(O)-$phenyl | 71 | $CH_3SO_3H \times \frac{1}{2} H_2O$ | 178–180 |
| 49 | $-CH_2-$ | 5-OH | $-H$ | 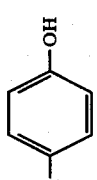 $-C(CH_3)_2-CH_2-$(4-OH-phenyl) | 72 | $HCl \times 1.5\ H_2O$ | 159–162 |
| 50 | $-CH_2-$ | 5-OH | $-C_2H_5$ |  $-CH_2-CH_2-$(4-NH-$SO_2CH_3$-phenyl) | | | |
| 51 | $-CH_2-$ | 5-OH | $-C_2H_5$ | 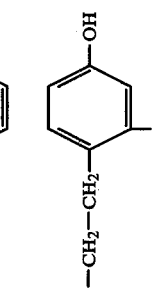 $-CH_2-CH_2-$(4-NH-C(O)-$CH_3$-phenyl) | | | |
| 52 | $-CH_2-$ | 5-OH | $-C_2H_5$ | $-CH_2-CH_2-$(4-$NH_2$-phenyl) | | | |
| 53 | $-CH_2-$ | 5-OH | $-C_2H_5$ |  $-CH_2-CH_2-$(3-$C_2H_5$-4-OH-phenyl) | | | |
| 54 | $-CH_2-$ | 5-O-C(O)-C-$(CH_3)_3$ | $-C_2H_5$ | $-CH(CH_3)_2$ | | | |

The following table shows compounds of the formula II which are used as starting materials for method A; they were prepared by the reaction sequence described above in connection with method A. These starting compound are themselves useful as pharmaceuticals because the have pharmacodynamic properties similar to those of the end products of the formula I.

TABLE IV

| Example No. | A | $R_1$ | $R_2$ | $R_3$ | Salt with | M.P. °C. |
|---|---|---|---|---|---|---|
| 55 | $-CH_2-$ | 5-OH | $-C_2H_5$ | $-CH(CH_3)_2$ | HCl × 2 H$_2$O | 240–242 |
| 56 | single bond | 4-OH | $-C_2H_5$ | $-CH(CH_3)_2$ | HCl | 218–222 |
| 57 | $-CH_2-$ | 6-OH | $-C_2H_5$ | $-CH(CH_3)_2$ | HCl | 250–254 |
| 58 | $-CH_2-$ | 6-OH | $-C_2H_5$ | $-C(CH_3)_3$ | HCl | 250–253 |
| 59 | single bond | 5-OH | $-C_2H_5$ | $-CH(CH_3)_2$ | HCl | 217–223 |
| 60 | $-CH_2-$ | 5-OH | $-C_2H_5$ | $-CH(CH_3)_2$ | HCl | 156–161 |
| 61 | $-CH_2-$ | 5-OH | $-CH_3$ | $-CH(CH_3)_2$ | HCl | 243–247 |
| 62 | $-CH_2-$ | 5-OH | $-C_2H_5$ | cyclopentyl | HCl | 254–258 |
| 63 | $-CH_2-$ | 5-OH | $-C_2H_5$ | cyclohexyl | HCl | 250 |

The compounds of the present invention, that is, those embraced by formula I above, in the form of their racemates, enantiomers or diastereoisomeric pairs of enantiomers, and their non-toxic, pharmacologically acceptable acid addition salts, have useful pharmacodynamic properties. More particularly, they exhibit bronchospasmolytic, spasmolytic and antiallergic activities, increase ciliary activity, and reduced inflamatory exudative reactions in warm-blooded animals. Therefore, the compounds of the instant invention are useful for the treatment of all forms of asthma and bronchitis, urticaria, conjunctivities, hay fever and the common cold. They also have a relaxing effect upon the uterine muscles, and are therefore useful for minimizing labor pains. The compounds are further useful for the treatment of cardiovascular disorder, such as high blood pressure, diseases of the pinpheral blood vessels and cardiac arrhythmia. Still other activities which have been observed are inhibition of gastic secretion and antidepressant effects in the CNS.

For the pharmacological tests, the usual test methods and test animals or organs were used. From a pharmacological point of view the compounds of the present invention are, in some respects, very different from commercially available products used for the same indications. In addition to having a good duration of effective action, they have a particularly sharp selectivity, for example, in their broncholytic effect in relation to the increase in heart rate. Thus, for example, for the compound of Example 1, in guinea pigs the ED$_{50}$ i.v. [g/kg] of the increase in heart rate is more than ten times the ED$_{50}$ i.v. [g/kg] of bronocholysis, which is only 0.045 g/kg. The absorption characteristics are generally favorable as well. Thus, the absorption quotient $$\frac{ED_{50}\ p.o.}{ED_{50}\ i.v.}$$

is only 1.1, for example, for the compound of Example 42 in Table III, which means that the oral activity is virtually as great as the intravenous activity. In the mouse, for example, the LD$_{50}$ values are so much higher than the therapeutic dose that a favorable therapeutic range is provided.

The therapeutic and prophylactic dosage depends upon the nature and gravity of the disorder and the route of administration.

In adults, the following dosages are recommended for the following indications:

As broncholytic, the compounds are administered orally in a dosage of from 0.05 to 5 mg, by inhalation from 0.1 to 1.0 mg and subcutaneously from 0.02 to 0.05 mg.

When used as uterine muscle relaxing agents, the compounds are administered orally in a dosage of from 10 to 50 mg or, in the form of a solution for infusion, 10 ml ampules containing from 0.01 to 1 mg are used.

For vasodilation, 20 to 100 mg are administered orally or ampules containing 20 to 40 mg are used for i.m. injection. As hypotensive agents, they are administered orally in a dose of from 200 mg to 1.8 g.

For pharmaceutical purposes the compounds of the present invention are administered to warm-blooded animals perorally, parenterally, rectally or topically as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories, lotions, creams, ointments, sprays or the like, and optionally other active ingredients.

Thus, as broncholytics they may be combined with theophyllines, parasympatholytics (e.g. ipratropium bromide), secretolytics (e.g. bromhexine), musculotropic spasmolytics (e.g. papaverine), corticosteroids or antillergics. When used as uterine relaxants, combinations with corticoids are possible.

Capsules, tablets, solutions and suspensions are suitable for oral administration. For pulmonary administration, preferably dry powders with a particle diameter of from 0.5 to 7 are introduced into the bronchial region by means of propellent gases. For parenteral administration, the preparation is preferably in the form of sterile isotonic aqueous solutions. For topical use, lotions, creams, ointments, emulsions and sprays are used.

The compounds according to the invention may also be used to increase the growth rate of meat-producing animals, such as pigs, cattle, sheep, chickens and geese. The utilization of the fodder is improved substantially and, furthermore, the meat is of a higher quality and has a lower fat content than when the new compounds are not used.

The following examples illustrate a few pharmaceutical compositions comprising a compound of the present invention as an active ingredient and represent the best modes contemplated of using the invention. The parts are parts by weight unless otherwise specified.

EXAMPLE 64

Tablets 220 mgm-tablets are prepared in conventional manner from the following ingredients:

| | |
|---|---|
| 5'-Hydroxy-8'-(1-hydroxy-2-isopropylamino-butyl)-2H—1,4-benzoxazin-3-(4H)—one | 20 parts |
| Colloidal silicic acid | 10 parts |
| Lactose | 118 parts |
| Potato starch | 60 parts |
| Polyvinylpyrrolidone | 6 parts |
| Na cellulose glycolate | 4 parts |
| Magnesium stearate | 2 parts |
| | 220 parts |

EXAMPLE 65

Injection solution 10 cc-ampules are filled with a solution prepared in conventional manner from the following ingredients:

| | |
|---|---|
| 5'-Hydroxy-8'-(1-hydroxy-2-isopropylamino-butyl)-2H—1,4-benzoxazin-3-(4H)—one | 10 parts |
| Sorbitol | 40 parts |
| Distilled water q.s. ad | 10,000 parts by vol. |

EXAMPLE 66

Suppositories 1700 mgm-rectal suppositories are prepared in conventional manner from the following ingredients:

| | |
|---|---|
| 5'-Hydroxy-8'-(1-hydroxy-2-isopropylamino-butyl)-2H—1,4-benzoxazin-3-(4H)—one | 100 parts |
| Suppository base (e.g. cocoa butter) | 1600 parts |
| | 1700 parts |

EXAMPLE 67

Inhalation powder

Hard gelatin capsules are filled with 20 mgm of a mixture prepared in conventional manner from the following ingredients:

| | |
|---|---|
| 5'-Hydroxy-8'-(1-hydroxy-2-isopropylamino-butyl)-2H—1,4-benzoxazin-3-(4H)—one | 0.5 parts |
| Lactose | 19.5 parts |
| | 20.0 parts |

Any one of the other compounds embraced by formula I or an non-toxic, pharmaceutically acceptable acid addition salt thereof may be substituted for the particular active ingredient in Examples 64 through 67. Likewise, the amount of active ingredient in these illustrative examples may be varied to achieve the dosage unit range set forth above, and the amounts and nature of the inert pharmaceutical carrier ingredients may be varied to meet requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

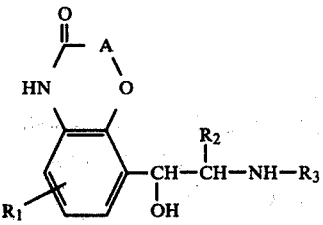

wherein
A is a single bond,

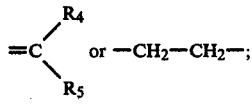

$R_1$ is —OH, —O—acyl or chlorine;
$R_2$ is hydrogen, methyl or ethyl;
$R_3$ is

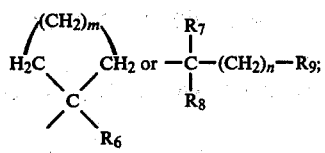

m is 2, 3 or 4;
n is 1, 2 or 3;
$R_4$ is hydrogen or lower alkyl;
$R_5$ is hydrogen, lower alkyl or, when $R_4$ is hydrogen, also phenyl;
$R_6$, $R_7$ and $R_8$ are each hydrogen or methyl;
$R_9$ is hydrogen, —Ar, —OAr or —NH—CO—Ar;
Ar is

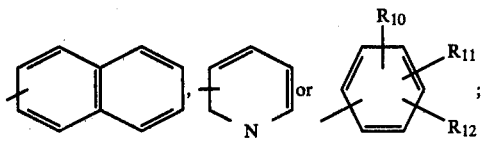

$R_{10}$, $R_{11}$ and $R_{12}$ which may be identical to or different from each other, are each hydrogen, hydroxyl, methyl, methoxy, halogen, methylenedioxy, —NH—$R_{13}$ or —CONH$_2$ and
$R_{13}$ is hydrogen, acyl or lower alkylsulfonyl; or a non-toxic, pharmaceutically acceptable acid addition salt thereof, in the form of their racemates, enantiomers or diastereoisomeric pairs of enantiomers.

2. A compound of claim 1, wherein A is a single bond, —CH$_2$—, —CH(CH$_3$)—, —C(CH$_3$)$_2$— or —CH(C$_2$H$_5$)—;
$R_1$ is methyl or ethyl;
$R_2$ is hydrogen, methyl or ethyl;
$R_3$ is

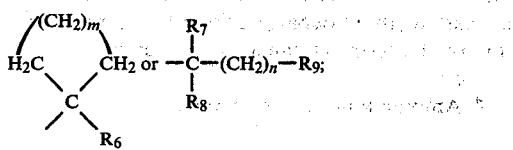

m is 2,3 or 4;

n is 1,2 or 3;

R$_6$, R$_7$ and R$_8$ are each hydrogen or methyl;

R$_9$ is hydrogen, —Ar or —NHCO—Ar;

Ar is 2-pyridyl, 4-pyridyl or

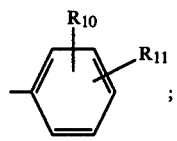

R$_{10}$ is hydrogen, hydroxy, methyl or, together with R$_{11}$, methylenedioxy; and R$_{11}$ is hydrogen, hydroxyl, methyl or, together with R$_{10}$, methylenedioxy;

or a non-toxic, pharmaceutically acceptable addition salt thereof.

3. A compound of claim 1, wherein A is —C(CH$_3$)$_2$— or —CH$_2$—;

R$_1$ is hydroxyl in the m- or p-position relative to the side chain;

R$_2$ is hydrogen, methyl or ethyl;

R$_3$ is isopropyl, tert.butyl, cyclopentyl, 1-methyl-cyclopentyl or

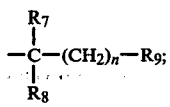

n is 1 or 2;

R$_7$ and R$_8$ are each hydrogen or methyl; and

R$_9$ is phenyl, 2-hydroxy-phenyl, 4-hydroxy-phenyl, 2-pyridyl, 4-pyridyl,

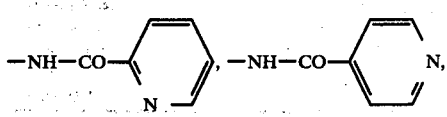

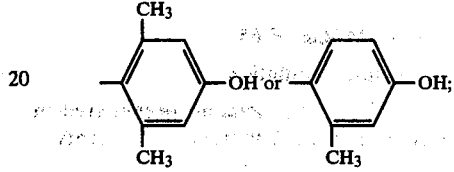

or a non-toxic, pharmaceutically acceptable acid addition salt thereof.

4. A compound of claim 1, which is 5′-hydroxy-8′-(1-hydroxy-2-isopropylamino-butyl)-2H-1,4-benzoxazin-3-(4H)-one or a non-toxic, pharmaceutically acceptable acid addition salt thereof.

5. A pharmaceutical composition for the treatment of asthma, bronchitis, urticaria, conjunctivities, hay fever, colds, cardiovascular disorders and uterine spasms, consisting essentially of an inert pharmaceutical carrier and an effective amount of a compound of claim 1.

6. The method of treating asthma, bronchitis, urticaria, conjunctivites, hay fever, colds, cardiovascular disorders and uterine spasma in a warm-blooded animal, which comprises perorally, parenterally, rectally or topically administering to said animal an effective amount of a compound of claim 1.

* * * * *

UNITED STATES PATENT AND TRADEMARK OFFICE
CERTIFICATE OF CORRECTION

PATENT NO. : 4,460,581
DATED     : July 17, 1984
INVENTOR(S) : KURT SCHROMM ET AL.

It is certified that error appears in the above-identified patent and that said Letters Patent is hereby corrected as shown below:

Column 1, lines 36 to 42, the formula

" 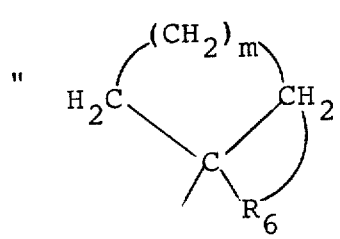 "   should read   -- 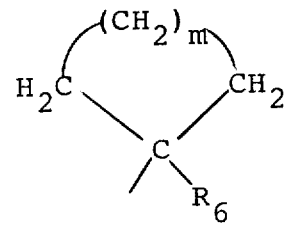 --

Column 11, line 23: "cataytic" should read -- catalytic --.

Column 12, line 31: "15" should read -- 15 ml --.

Signed and Sealed this

Seventh Day of May 1985

[SEAL]

Attest:

DONALD J. QUIGG

Attesting Officer    Acting Commissioner of Patents and Trademarks